United States Patent [19]

Virnig et al.

[11] Patent Number: 4,626,582

[45] Date of Patent: Dec. 2, 1986

[54] ACRYLOXYMETHYL SUBSTITUTED FATTY COMPOUNDS

[75] Inventors: Michael J. Virnig, Fridley; James P. Clark, St. Anthony; Edward D. DiDomenico, Anoka, all of Minn.

[73] Assignee: Henkel Corporation, Minneapolis, Minn.

[21] Appl. No.: 706,549

[22] Filed: Feb. 28, 1985

[51] Int. Cl.$^4$ .............................................. C08F 20/36
[52] U.S. Cl. ................................... 526/298; 526/304; 526/320; 526/321; 558/444; 560/185; 560/205; 560/222; 564/224
[58] Field of Search ............... 526/298, 304, 320, 321; 560/222, 205, 185; 564/224; 558/444

[56] References Cited

U.S. PATENT DOCUMENTS

| | | | |
|---|---|---|---|
| 4,216,343 | 8/1980 | Rogier | 568/853 |
| 4,243,818 | 1/1981 | Rogier | 560/224 |
| 4,356,128 | 10/1982 | Rogier | 260/465.6 |

Primary Examiner—Paul R. Michl
Attorney, Agent, or Firm—Ernest G. Szoke; John Daniel Wood

[57] ABSTRACT

Acryloxymethyl fatty compounds are provided which are useful as monomers in the preparation of radiation curable coatings. The preferred compounds are acrylate or methacrylate esters of 9(10)-(hydroxymethyl)-stearonitrile, 9(10)-(hydroxymethyl)-N,N-dimethyl-stearamide, methyl 9(10)-(hydroxymethyl)-stearate, N-acetyl-N-methyl 9(10)-(hydroxymethyl)-nonadecanamine, 9(10)-cyano-octadecanol, 9(10)-(carboxydimethylamino)octadecanol, 9(10)-(carboxymethyoxy)octadecanol and 9(10)-(N-acetyl-N-methylaminomethyl)octadecanol.

24 Claims, No Drawings

ACRYLOXYMETHYL SUBSTITUTED FATTY COMPOUNDS

FIELD OF THE INVENTION

This invention relates to new compositions of matter which contain an acryloxymethyl moiety. More particularly, this invention relates to acrylate esters of hydroxyl-substituted fatty compounds that are also nitriles, amides, or esters.

BACKGROUND OF THE INVENTION

U.S. Pat. No. 4,356,128 to Rogier discloses that hydroxymethyl fatty nitriles, hydroxymethyl fatty amides, and hydroxymethyl fatty esters are useful as polyols for preparing polyurethane coatings and paints.

U.S. Pat. No. 4,216,343 to Rogier describes the preparation of hydroxymethyl fatty alcohols and the use thereof with polyisocyanates to form polyurethanes.

U.S. Pat. No. 4,243,818 to Rogier discloses acrylate esters of gem-bis(hydroxymethyl) fatty alcohols and hydroxymethyl fatty alcohols and the use thereof in the preparation of radiation curable coatings.

SUMMARY OF THE INVENTION

This invention relates to acryloxymethyl fatty compounds having the structural formula:

$$CH_3-(CH_2)_m-((Y)-C-(Z)-(CH_2)_n-X$$

wherein:

m and n are integers, provided that n is greater than 3 and the sum of m and n ranges from 7 to 19;

Y is a hydrogen, methylol or acryloxymethyl group; and one of X and Z is acryloxymethyl and the other is selected from the group of:

(a) —CN,
(b) —C(O)—NR$^1$R$^2$,
(c) —C(O)—OR$^3$, and
(d) —CH$_2$—NR$^4$R$^5$ wherein: R$^1$ R$^2$ and R$^3$ are independently lower alkyl provided that R$^1$ and R$^2$ may together constitute a divalent hydrocarbon group having 4, 5, or 6 aliphatic carbon atoms or 3,4, or 5 aliphatic carbon atoms and one hetero atom or group; R$^4$ is lower acyl; and R$^5$ is hydrogen or lower alkyl; provided that when X is acryloxymethyl, Y is hydrogen.

This invention also relates to compounds having the above formula wherein X is —CH$_2$—NR$^4$R$^5$ but Z is hydroxymethyl (—CH$_2$OH) rather than acryloxymethyl as required above. These compounds are novel precursors for the compounds defined above wherein X is —CH$_2$—NR$^4$R$^5$ and Z is acryloxymethyl.

As used herein, the term acryloxymethyl is intended to be generic to substituents of the formula:

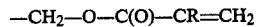

—CH$_2$—O—C(O)—CR=CH$_2$ wherein R is hydrogen or methyl, i.e. the compounds of this invention are acrylate or methacrylate esters. The term acyl is intended to be generic to the residue of saturated lower organic carboxylic acids such as acetic and propionic acids. The term "lower", when applied to an alkyl, alkylene or acyl group, is used to denote a group having from 1 to about 4 aliphatic carbon atoms.

The preferred compounds of this invention are those wherein m and n are each 7 or 8 and the sum of m and n are 15 (i.e. those derived from oleonitrile, an oleamide, an oleic acid ester, oleyl amine, or oleyl alcohol);

R is hydrogen, each R$^1$ and R$^2$ is methyl or R$^1$ and R$^2$ together constitute a —CH$_2$—CH$_2$—O—CH$_2$—CH$_2$— group, R$^3$ is methyl, R$^4$ is acetyl and R$^5$ is methyl.

This invention also relates to the use of the compounds defined above to prepare curable coatings.

DETAILED DESCRIPTION OF THE INVENTION

The following detailed description will describe the preparation of the acrylates of this invention, the preparation of the hydroxymethyl fatty compounds useful as starting materials in the preparation of the acrylates of this invention, and the preparation of curable coatings from the acrylates of this invention.

A. Acrylate Preparation

The acryloxymethyl fatty compounds of this invention are prepared by reacting the corresponding hydroxyl-substituted fatty compound with an acryloyl compound that is capable of esterifying the respective hydroxymethyl compound. The hydroxymethyl fatty compounds have the general formula:

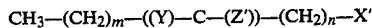

$$CH_3-(CH_2)_m-((Y)-C-(Z'))-(CH_2)_n-X'$$

wherein m, n, X and Y are as previously defined and one of X' and Z' is hydroxymethyl and the other is selected from the group previously defined for X and Z. Methods of obtaining these hydroxyl-substituted fatty compounds are discussed below.

The acryloyl compounds used to esterify the hydroxymethyl fatty compound is preferably an acryloyl halide, such as acryloyl chloride, but may be other reactive acryloyl compounds, such as acryloyl anhydride, acrylic acid or lower alkyl esters thereof.

The amount of acryloyl compound used to esterify the hydroxymethyl fatty polyol will depend, in part, on the nature of the hydroxymethyl fatty polyol and the product desired. When a di-acryloxymethyl compound of this invention is desired, i.e. a compound wherein y is acryloxymethyl, an amount of the acryloyl compound in excess of 2 equivalents thereof should be used to ensure the full acrylation of the starting gem-bis(hydroxymethyl) fatty compound. When a nonhydroxyl-containing monoacryloxymethyl compound of this invention is desired, i.e. a compound wherein Y is hydrogen, an amount of the acryloyl compound in excess of 1 equivalent thereof should be used to ensure the full acrylation of the starting hydroxymethyl fatty compound.

When a hydroxymethyl acryloxymethyl fatty compound of this invention is desired, i.e. a compound wherein Y is hydroxymethyl, a single equivalent of the acryloyl compound should be used in conjunction with techniques to control the reaction to conditions to ensure completion of the reaction. For example, when the acryloyl compound is acrylic acid, it is convenient to remove the water that is a by-product of the acrylation reaction by techniques such as azeotropic distillation and thereby force the reaction to completion.

When the starting hydroxymethyl fatty compound is a hydroxymethyl fatty ester, i.e. when X is —C(O)—OR$^3$, the starting fatty ester may self trans-esterify when subjected to certain reaction conditions chosen. One or more steps can be taken to minimize this self trans-esterification. For example, (1) a large excess of the acryloyl compound may be used, (2) the concentration of the hydroxymethyl fatty ester in the reaction medium can be kept low, and (3) highly reactive acryloyl compounds can be used to reduce the total reaction time and thereby reduce the time for trans-esterification.

B. Preparation of Starting Materials

The hydroxymethyl fatty nitriles, amides and esters useful as starting materials in preparing the compounds of the present invention wherein Z is acryloxymethyl, may be prepared as described in U.S. Pat. No. 4,356,128 to Rogier, incorporated herein by reference thereto. Briefly, an unsaturated fatty nitrile, amide, or ester is hydroformylated, i.e. reacted with carbon monoxide and hydrogen in the presence of a rhodium catalyst to produce a formyl substituted fatty nitrile, amide, or ester. This formyl substituted compound can then be simply reduced to the corresponding alcohol to prepare the monohydroxymethyl fatty compounds useful as starting materials, i.e. compounds wherein Y is hydrogen. When a gem-bis(hydroxymethyl) fatty compound is desired, the formyl substituted compound is used in the Tollen's reaction to produce a gem-bis(hydroxymethyl) compound. For example, oleonitrile can be reacted with carbon monoxide and hydrogen in the presence of a rhodium catalyst to produce a 9(10)-formyloctadecanonitrile which can in turn be reacted with 2 equivalents of formaldehyde in the presence of sodium hydroxide to produce 9,9(10,10)-bis(hydroxymethyl)octadecanonitrile.

When an amide of a fatty amine is desired, i.e. a compound wherein X is —$CH_2$—$NR^4R^5$, it is convenient to acylate and, optionally, alkylate a compound such as oleyl amine and then hydroformylate and acrylate as described above. For example, oleyl amine can be acetylated with acetic acid and methylated to form N-acetyl-N-methyl oleyl amine. This unsaturated amine can then be reacted with carbon monoxide and hydrogen to prepare N-acetyl-N-methyl-10(11)-formyl octadecanamine. This formylated amine can then be reduced to prepare N-acetyl-N-methyl-10(11)-hydroxymethyloctadecanamine which is finally reacted with an acryloyl compound to prepare N-acetyl-N-methyl-10(11)-acryloxymethyloctadecacamine.

When compounds wherein X is acryloxymethyl are desired, the synethesis is conveniently accomplished by hydroformylating an unsaturated fatty alcohol to prepare a formyl-substituted fatty alcohol. The formyl-substituted fatty alcohol can then undergo a reductive amination and acylation to prepare a compound wherein X is —$CH_2$—OH and Z is —$CH_2$—$NR^4R^5$ which can then be acrylated as described above. For example, oleyl alcohol can be reacted with carbon monoxide and hydrogen to prepare 9(10)formyloctadecanol which can in turn be reacted with methylamine and hydrogen in the presence of Rainy Nickel to prepare 9(10)-(N-methhylaminomethyl)octadecanol. This amino alcohol can then be reacted with acetic acid to prepare 9(10)-(N-acetyl-N-methyl aminomethyl)octadecanol which can, in turn be reacted with an acryloyl compound to prepare 9(10)-(N-acetyl-N-methylaminomethyl)octadecanyl acrylate.

When compounds wherein Z is cyano, carboxydialkylamino, or carboxyalkoxy are desired, it is convenient to oxidize the formyl group of the formyl-substituted fatty alcohol to prepare a carboxy-substituted fatty alcohol. The carboxyl group of the carboxy-substituted fatty alcohol can then be derivatized to form a cyano group, a carboxydialkylamino group, or a carboxyalkoxy group. For example, 9(10)-formyloctadecanol can be reacted with ammonia in the presence of zinc oxide to prepare 9(10)-cyano-octadecanol, which can be reacted with an acryloyl compound to prepare 9(10)-cyano-octadecanyl acrylate. The 9(10)-carboxy-octadecanol can also be reacted (a) with dimethylamine to prepare 9(10)-(carboxydimethylamino)octadecanol which can, in turn, be reacted with an acryloyl compound to prepare 9(10)-(carboxydimethylamino)octadecanyl acrylate, or (b) with methanol and then an acryloyl compound to prepare 9(10)-(carboxymethoxy)octadecanyl acrylate.

C. Coating Preparation

The acryloxymethyl fatty compounds of this invention are useful as monomers in the preparation of polymeric coatings. The compounds of this invention can be homopolymerized or the compounds can be mixed with unsaturated monomers to form a composition of comonomers which can then be polymerized. A composition of this invention is applied to a substrate such as wood, metal, paper, or plastics by any convenient method such as knife, blade, brush, dip or spray. The coated surface can then be exposed to radiation to cure the composition through the radiation sensitive pi bonds. The coating is cured by the addition polymerization of the components of the composition. Suitable sources of ionizing radiation include ultraviolet light or radioactive sources such as are described in U.S. Pat. No. 3,935,330 to Smith et al.

The coating can also be cured by including in the composition free radical initiators such as benzoin, benzoin ethers, and Michler's Ketone. Other suitable free radical initiators are organic peroxides, hydroperoxides, per acids, per esters, azo compounds, ditertiary butyl peroxide, benzoyl peroxide, 2,4-dichlorobenzoyl peroxide, tertiary butyl hydroperoxide, 2,5-dimethyl-2,5-bis(hydroxyperoxy)-hexane, peracetic acid, perbenzoic acid, tertiary butyl peroxypivalate, tertiary butyl peracetic acid and azo-bis-isobutyl nitrile. The free radical initiator may be present at from 0.01 to about 20% by weight of the radiation curable components.

To ensure that the composition does not polymerize prior to the application of the composition to a substrate, a free radical inhibitor may be added to the composition. Examples of suitable inhibitors include hydroquinone and the methyl ether thereof or butylated hydroxy toluene at a level of from about 5 ppm to about 2000 ppm by weight of the radiation curable components.

The amount of radiation necessary to cure the composition will of course depend upon the wavelength and intensity of the radiation, the angle of exposure to the radiation, the thickness of the coating to be applied, and the amount of acryloxymethyl fatty compound in the coating composition as well as the presence or absence of a free radical initiating catalyst. For any given composition, experimentation to determine the amount of radiation sensitive pi bonds not cured following exposure to the radiation source is the best method of determining the amount and duration of the radiation required.

The coatings produced by the cure of the acryloxymethyl fatty compounds of this invention are useful in a wide variety of applications i.e. decorative, maintenance, or industrial coatings. For example, they can be used as binders in inks. In the electronics area, these materials have applications as non-conductive coatings, e.g. solder masks for circuit boards or moisture resistant coatings for circuit boards or optical fibers.

The use of the acryloxymethyl fatty compounds of this invention should provide excellent flexibility in the final coating and offer good compatibility with other compounds in the coating formulation. The presence of the polar nitrile, amide, or ester functionality will also lead to improved surface wetting properties as compared with most commercially available curable coatings resulting in better adhesion to the substrate and improved pigment compatibility.

The hydroxyl-substituted mono-acryloxymethyl fatty compound should also have application as raw materials for the preparation of crosslinked copolymers. The reaction of the hydroxyl-substituted monoacryloxymethyl fatty compounds and a polyol with a polyfunctional organic compound copolymerizable therewith, e.g. polybasic acids or polyisocyanates will yield an acrylate terminated copolymer, e.g. a polyester or a polyurethane, which can then be cured by addition polymerization of the acrylate terminal groups to form a crosslinked polymer. These copolymers are especially useful when cured on a substrate to form a crosslinked polymeric coating.

EXAMPLES

The following examples illustrate methods which may be used to prepare acryloxymethyl fatty compounds.

EXAMPLE 1

Preparation of 9(10)-(acryloxymethyl)stearonitrile

Charge

| Materials | M.W. | Weight (g) | Moles |
| --- | --- | --- | --- |
| 9(10)-Hydroxymethylstearonitrile | 295 | 200 | 0.68 |
| Acrylic Acid | 72 | 63.6 | 0.88 |
| Hydroquinone | 110 | 8 | 0.073 |
| p-Toluenesulfonic acid | 190 | 6 | 0.032 |
| Heptane | 100 | 205 | 2.05 |

Equipment

A three neck one liter round-bottom flask fitted with magnetic stirrer, Dean-Stark trap for azeotropic removal of water, vacuum regulator, and capillary tube fitted so that a small stream of air could be continuously introduced beneath the surface of the liquid.

Procedure

The materials were charged to the flask and the pressure was adjusted to 350 mm of Mercury. The reaction mixture was then heated to reflux. After 6.5 hours, 86.8% of the theoretical amount of water had been collected. The reaction mixture was cooled and poured into a separatory funnel containing 200 mls of heptane. At an O/A of 1, the organic phase was then washed once with warm water, twice with 2% potassium hydroxide, and then four times with deionized water until neutral. The organic phase was then filtered and the heptane was removed in vacuo to give approximately 200 g of an oil. Thin film IR indicated the presence of the desired product and some residual starting material.

EXAMPLE 2

Preparation of 9(10)-(Methacryloxymethyl)Stearonitrile

Charge

| Materials | M.W. | Weight (g) | Moles |
| --- | --- | --- | --- |
| 9(10)-Hydroxymethylstearonitrile | 295 | 100 | 0.34 |
| Methacrylic Acid | 86 | 57.8 | 0.67 |
| Hydroquinone | 110 | 8 | 0.073 |
| p-Toluenesulfonic acid | 190 | 6 | 0.032 |
| Heptane | 100 | 205.6 | 1.03 |

Procedure

The reaction was carried out in the same fashion as described in Example 1 with the following modifications. Initially, only 91% of the methacrylic acid was charged to the flask. After seven hours at reflux, the pressure was adjusted to atmospheric and the remainder of the methacrylic acid was added. After an additional six hours at reflux, the reaction mixture was cooled and worked up as previously described to yield 115.2 g of an oil. That the composition contained the desired product was confirmed by IR and NMR spectroscopy.

EXAMPLE 3

Preparation of a Mixture of 9(10)-Bis(Acryloxymethyl)Stearonitrile and 9(10)-Hydroxymethyl-9(10)-Acryloxymethylstearonitrile Charge

| Materials | M.W | Weight (g) | Moles |
| --- | --- | --- | --- |
| 9(10)-Bis(hydroxymethyl)stearonitrile | 325 | 100 | 0.31 |
| Acrylic Acid | 72 | 48.7 | 0.67 |
| p-methoxyphenol | 124 | 4 | 0.032 |
| p-Toluenesulfonic acid | 190 | 3 | 0.016 |
| Heptane | 100 | 68.4 | 0.68 |

Equipment

A three neck 500 ml round bottom flask was fitted with a magnetic stirrer, Dean-Stark trap for azeotropic water removal, vacuum regulator, and capillary tube positioned so that a small stream of air was continuously introduced beneath the surface of the liquid.

Procedure

The materials were charged to the flask and the pressure was adjusted to 350 mm of mercury. The reaction mixture was then heated to reflux. After 9 hours of reflux, 89% of the theoretical amount of water had been collected. The reaction mixture was then cooled and then poured into a separatory funnel containing 100 ml of heptane. The resultant organic was then given the following series of aqueous washes at a O/A of 1: warm tap water, 2% sodium hydroxide, warm tap water, 2% sulfuric acid, and then deionized water until neutral. During the course of the washes, a small portion of ethyl acetate was added to the organic phase to improve the solubility of the product. The organic phase was then filtered and the heptane removed in vacuo to yield 113.7 g of an oil. The hydroxyl value of the product indicated that the material contained 23% of the monoacrylate and 77% of the diacrylate.

EXAMPLE 4

Preparation of N,N-Dimethyl-9(10)-(Acryloxymethyl)Stearamide

Charge

| Materials | M.W. | Weight (g) | Moles |
|---|---|---|---|
| N,N,—Dimethyl-9(10)-Hydroxy-methylstearamide | 345 | 200 | 0.58 |
| Acryloyl Chloride | 90 | 79.2 | 0.88 |
| Triethylamine | 101 | 88.8 | 0.88 |
| Phenothiazine | — | 0.1 | — |
| Dichloromethane | 84 | 927.5 | 11.04 |

Procedure

The reaction was carried out in the same fashion as described in Kulkarni et al. JAOCS, 46, 396 (1969). The reaction mixture was worked up in the following fashion. The reaction mixture was poured into 1000 ml of heptane and allowed to stand overnight. The precipitated triethylamine hydrochloride was removed by filtration. The organic was then given a series of aqueous washes. At an O/A of 1, the organic was washed once with water, three times with 2% sulfuric acid, once with water, once with 2% potassium hydroxide, once with water, once with 2% sulfuric acid, and then deionized water washed to neutrality. The organic was filtered and the solvent removed in vacuo to yield 217.8 g of an oil. That the composition contained the desired product was confirmed by IR and NMR spectroscopy.

EXAMPLE 5

Preparation of 4-[9(10)-Acryloxymethylstearoyl]Morpholine

| Materials | M.W. | Weight (g) | Moles |
|---|---|---|---|
| 4-[9(10-Hydroxymethylstearoyl] morpholine | 385 | 200 | 0.52 |
| Acryloyl Chloride | 90 | 70.2 | 0.78 |
| Triethylamine | 101 | 78.8 | 0.78 |
| Phenothiazine | 190 | 0.1 | — |
| Dichloromethane | 84 | 927.5 | 11.04 |

Procedure

The procedure was identical to that of Example 4. There was obtained 208.1 g of an oil. That the composition contained the desired product was confirmed by IR and NMR spectroscopy.

EXAMPLE 6

Preparation of Methyl 9(10)-Acryloxymethylstearate

Charge

| Materials | M.W. | Weight (g) | Moles |
|---|---|---|---|
| Methyl 9(10)-hydroxymethyl-stearate | 328 | 200 | 0.61 |
| Acrylic Acid | 72 | 48.3 | 0.67 |
| p-Methoxyphenol | 124 | 4 | 0.03 |
| p-Toluenesulfonic acid | 190 | 3 | 0.016 |
| Heptane | 100 | 64.8 | 0.65 |

Equipment

A one liter 3-neck round bottom flask fitted with magnetic stirrer, thermometer, Dean-Stark assembly for azeotropic water removal, and a vacuum regulator. Flask was also fitted with a capillary tube in such a manner that a small stream of air could be drawn through the liquid in the pot during the reaction.

Procedure

The materials were charged into the flask and the pressure adjusted to 400 mm of Hg. The contents were then heated to reflux. After four hours at reflux, no additional aqueous phase collected in the decanter. Approximately 1.4 times the theoretical amount of water was collected as aqueous phase in the Dean-Stark trap. The contents of the flask were cooled to room temperature and poured into a separatory funnel with an additional 64.8 g of heptane. The organic phase was then washed with water, 2% sodium hydroxide, water, 2% sulfuric acid, and then deionized water at an O/A of 1. Severe emulsions were encountered during the workup. The organic was the filtered and the heptane removed in vacuo to yield 196.9 g of a light yellow oil. That the composition contained the desired product was confirmed by NMR and IR spectroscopy.

The aqueous decanted during the reaction contained approximately 16–17% methanol. This indicates that approximately 12% of the available ester functionality in the starting material had undergone trans-esterification to give polyester acrylates.

What is claimed is:

1. A compound having the structural formula:

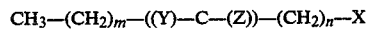

wherein:
m and n are integers, provided that n is greater than 3 and the sum of m and n ranges from 7 to 19;
Y is a hydrogen, methylol or acryloxymethyl group; and one of X and Z is acryloxymethyl and the other is selected from the group of:
(a) —CN,
(b) —C(O)—NR$^1$R$^2$,
(c) —C(O)—OR$^3$, or
(d) —CH$_2$—NR$^4$R$^5$ wherein: R$^1$ R$^2$ and R$^3$ are independently lower alkyl provided that R$^1$ and R$^2$ may together constitute a divalent hydrocarbon group having 4, 5, or 6 aliphatic carbon atoms or 3,4, or 5 aliphatic carbon atoms and one hetero atom or group; R$^4$ is lower acyl; and R$^5$ is hydrogen or lower alkyl; provided that when X is acryloxymethyl, Y is hydrogen.

2. A compound in accordance with claim 1 wherein Z is acryloxymethyl.

3. A compound in accordance with claim 2 wherein X is —CN.

4. A compound in accordance with claim 3 wherein Y is hydrogen, R is hydrogen and m and n are 7 or 8 provided that the sum of m and n is 15.

5. A compound in accordance with claim 2 wherein X is —C(O)—NR$^1$R$^2$.

6. A compound in accordance with claim 5 wherein R$^1$ and R$^2$ are both lower alkyl.

7. A compound in accordance with claim 5 wherein R$^1$ and R$^2$ are both methyl.

8. A compound in accordance with claim 5 wherein R$^1$ and R$^2$ are methyl, Y is hydrogen, R is hydrogen and m and n are 7 or 8 provided that the sum of m and n is 15.

9. A compound in accordance with claim 5 wherein R$^1$ and R$^2$ constitute a divalent hydrocarbon group having 4, 5, or 6 aliphatic carbon atoms or 3, 4 or 5 aliphatic carbon atoms and one hetero atom or group.

10. A compound in accordance with claim 9 wherein $R^1$ and $R^2$ constitute a group having the formula: $-CH_2-CH_2-O-CH_2-CH_2-$.

11. A compound in accordance with claim 2 wherein X is $-C(O)-OR^3$.

12. A compound in accordance with claim 11 wherein $R^3$ is methyl.

13. A compound in accordance with claim 2 wherein X is $-CH_2-NR^4R^5$.

14. A compound in accordance with claim 13 wherein $R^4$ is acetyl and $R^5$ is methyl.

15. A compound in accordance with claim 14 wherein Y is hydrogen, R is hydrogen and m and n are 7 or 8 provided that the sum of m and n is 15.

16. A compound in accordance with claim 1 wherein X is acryloxymethyl.

17. A compound in accordance with claim 1 wherein Y is hydrogen.

18. A compound in accordance with claim 1 wherein Y is methylol.

19. A compound in accordance with claim 1 wherein Y is acryloxymethyl.

20. A compound in accordance with claim 1 wherein n is 7 or greater.

21. A method of forming a coating comprising the curing of a compound in accordance with claim 1.

22. A polymeric coating which contains as a monomeric unit a compound in accordance with claim 1.

23. A compound having the structural formula:

$$CH_3-(CH_2)_m-((Y)-C-(CH_2-OH))-(CH_2)_n-NR^4R^5$$

wherein:
m and n are integers provided that n is greater than 3 and the sum of m and n ranges from 8 to 20;
Y is hydrogen, methylol or acryloxymethyl;
$R^4$ is lower acyl; and
$R^5$ is hydrogen or lower alkyl.

24. A compound in accordance with claim 23 wherein m is 7 or 8, n is 8 or 9 and the sum of m and n is 16.

* * * * *